US012721815B2

(12) United States Patent
Parvanian

(10) Patent No.: US 12,721,815 B2
(45) Date of Patent: Sep. 1, 2026

(54) FREEZE-DRIED EXOSOME COMPOSITION AND USES THEREOF

(71) Applicant: AVECIN-Biopharma Oy, Turku (FI)

(72) Inventor: Sepideh Parvanian, Turku (FI)

(73) Assignee: AVECIN-Biopharma Oy, Turku (FI)

( * ) Notice: Subject to any disclaimer, the term of this patent is extended or adjusted under 35 U.S.C. 154(b) by 795 days.

(21) Appl. No.: 18/159,352

(22) Filed: Jan. 25, 2023

(65) Prior Publication Data

US 2023/0285302 A1 Sep. 14, 2023

(30) Foreign Application Priority Data

Mar. 9, 2022 (FI) .................................... 20225204

(51) Int. Cl.

| | |
|---|---|
| ***A61K 9/19*** | (2006.01) |
| ***A61K 8/60*** | (2006.01) |
| ***A61K 8/73*** | (2006.01) |
| ***A61K 8/9789*** | (2017.01) |
| ***A61K 31/12*** | (2006.01) |
| ***A61K 47/26*** | (2006.01) |
| ***A61K 47/36*** | (2006.01) |
| ***A61Q 19/00*** | (2006.01) |

(52) U.S. Cl.

CPC .................. *A61K 9/19* (2013.01); *A61K 8/60* (2013.01); *A61K 8/735* (2013.01); *A61K 8/9789* (2017.08); *A61K 31/12* (2013.01); *A61K 47/26* (2013.01); *A61K 47/36* (2013.01); *A61Q 19/00* (2013.01); *A61K 2800/87* (2013.01)

(58) Field of Classification Search

CPC . A61K 9/19; A61K 8/60; A61K 8/735; A61K 8/9789; A61K 31/12; A61K 47/26; A61K 47/36; A61K 2800/87; A61K 8/14; A61K 9/0014; A61K 9/5184; A61K 2800/84; A61Q 19/00; A61Q 19/08

See application file for complete search history.

(56) References Cited

FOREIGN PATENT DOCUMENTS

| | | | |
|---|---|---|---|
| CN | 100361709 | C | 1/2008 |
| CN | 112451488 | A | 3/2021 |
| CN | 113171332 | A | 7/2021 |

OTHER PUBLICATIONS

Li et al. (CN111840127A Machine English Translation) (Year: 2020).*

Aqil et al., “Exosomes for the Enhanced Tissue Bioavailability and Efficacy of Curcumin”, Published online Oct. 18, 2017, The AAPS Journal, vol. 19, No. 6, Nov. 2017 pp. 1691-1702 DOI: 10.1208/s12248-017-0154-9, 12 pages.

Finnish Patent and Registration Office, Search Report, Patent Application No. 20225204, mailed Sep. 21, 2022, 2 pages.

Gurruchaga et al. “Low molecular-weight hyaluronan as a cryoprotectant for the storage of microencapsulated cells” Available Online Jun. 30, 2018, International Journal of Pharmaceutics, vol. 548, No. 1, https://doi.org/10.1016/j.jpharm.2018.06.066, 11 pages.

* cited by examiner

*Primary Examiner* — Robert A Wax

*Assistant Examiner* — Quanglong N Truong

(74) *Attorney, Agent, or Firm* — Ziegler IP Law Group, LLC.

(57) ABSTRACT

The invention relates to compositions and methods for exosome preservation by freeze-drying as well as methods of use of the freeze-dried exosome compositions.

19 Claims, 15 Drawing Sheets

(a)

(b)

(c)

(a)

(b)

(c)

FREEZE-DRIED EXOSOME COMPOSITION AND USES THEREOF

TECHNICAL FIELD

The present disclosure relates generally to extracellular vesicles, in particular (plant derived) exosomes, their isolation, preservation, formulation and uses thereof, including cryoprotectants for exosomes, freeze-dried exosome composition, production process for such exosome compositions as well as methods of use and formulations and devices for applying such exosome compositions.

BACKGROUND

Cryopreservation of exosomes at −20° C. or −80° C. is the most common method to preserve exosomes' activity with a shelf life of a maximum of one year. However, freeze-drying or lyophilization is currently considered to be the more reliable method to preserve extracellular vesicles (EVs). Lyophilization may significantly extend the stability and shelf life of the EVs while it lowers storage demands and costs. To prevent EVs from damages during lyophilization, various cryoprotectants have been used such as different kinds of sugars like trehalose, mannitol, sucrose, lactose, glucose, saccharose, maltose, polyvinylpyrrolidone Despite recent developments, there is an ongoing need in the art for high-performance preservation methods for the manufacture of exosome preparations that facilitate their use, especially to facilitate storage at ambient temperatures.

SUMMARY

The present disclosure provides a cryoprotectant for exosomes comprising trehalose and low molecular weight hyaluronic acid having molecular weight lower than 10 kDa. The cryoprotectant identified by the inventors allows for increased viability of the exosomes upon storage at low temperature as well as following freeze-drying a composition comprising the exosomes and the cryoprotectant, and, allowing for subsequent storage at ambient temperature.

The present disclosure further provides a freeze-dried composition comprising exosomes, low molecular weight hyaluronic acid having molecular weight lower than 10 kDa and trehalose.

The present disclosure further provides production process for a freeze-dried composition comprising the steps of:

(a) providing an exosome containing liquid, (b) combining the exosome containing liquid with a cryoprotectant comprising trehalose and LMW HA to obtain a combined exosome cryoprotectant preparation, and, (c) freeze drying the combined exosome cryoprotectant preparation.

The freeze-dried composition is typically useful in cosmeceutical applications, e.g. as a component of a skincare product.

DETAILED DESCRIPTION OF EMBODIMENTS

Figure 1A:
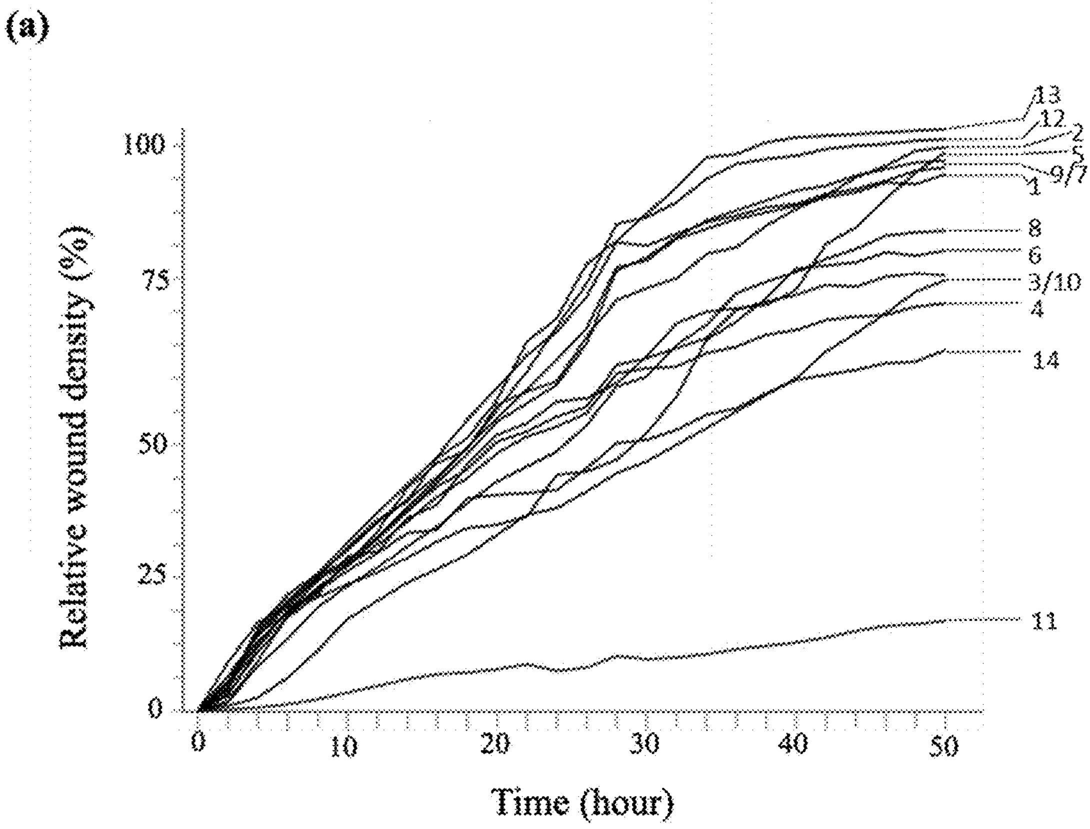
FIGS. 1A-1B illustrate the effect on (a) relative wound density comparison of human dermal fibroblasts incubated with exosomes during 50 hours and (b) relative wound density quantification after 24 hours incubation for exosomes from different plant sources and determined as described in example 8.1.

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a cryoprotectant for exosomes comprising trehalose and low molecular weight hyaluronic acid having molecular weight lower than 10 kDa.

The present disclosure further provides a freeze-dried composition comprising exosomes, low molecular weight hyaluronic acid having molecular weight lower than 10 kDa and trehalose.

The present disclosure further provides production process for a freeze-dried composition comprising the steps of:

(a) providing an exosome containing liquid,
(b) combining the exosome containing liquid with a cryoprotectant comprising trehalose and LMW HA to obtain a combined exosome cryoprotectant preparation, and,
(c) freeze drying the combined exosome cryoprotectant preparation.

In one embodiment, the present disclosure provides a cryoprotectant for exosomes comprising trehalose and low molecular weight hyaluronic acid (LMW HA) having molecular weight lower than 10 kDa. The inventors found that the combination of LMW HA having molecular weight lower than 10 kDa and trehalose is favourable for the purpose of cryopreservation of exosomes, in particular plant derived exosomes, providing for increased stability. Exosomes maintain their structural and/or functional integrity upon storage at low temperature in the presence of the cryoprotectant. Furthermore, it has been found that a synergy is achieved by combined use of lower than 10 kDa molecular weight hyaluronic acid and trehalose in cryoprotection of plant exosomes, as higher exosome concentration and better morphology in lyophilization is achieved. Also, the combination of trehalose and LMW HA with molecular weight lower than 10 kDa while preventing aggregation during lyophilization, resulted in a smaller, homogenous, and higher concentration of exosomes. The molecular weight of hyaluronic acid may be lower than 10, 9, 8, 7, 6, 5, 4, 3, 2, 1 kDa.

As used herein, "cryoprotectant" and in particular "cryoprotectant for exosomes" refer to a composition comprising compounds that allow for preservation of EVs, in particular exosomes, at low temperatures. As used herein, "low temperature" is below −20° C., below −30° C., below −40° C., below −50° C., below −60° C., below −70° C. or below −80° C.

The low molecular weight hyaluronic acid (LMW HA) as used herein, refers to hyaluronic acids having molecular weight lower than 10 kDa. The molecular weight of hyaluronic acid as used herein may be lower than 10, 9, 8, 7, 6, 5, 4, 3, 2, 1 kDa.

These effects on viability were also, if not more, present following freeze-drying of a composition comprising exosomes, in particular plant derived exosomes, and the cryoprotectant comprising trehalose and LMW HA. Consequently, in a further embodiment, a freeze-dried composition comprising exosomes, low molecular weight hyaluronic acid (LMW HA) having molecular weight lower than 10 kDa and trehalose is provided. In an embodiment, exosomes are plant derived exosomes. The molecular weight of hyaluronic acid may be lower than 10, 9, 8, 7, 6, 5, 4, 3, 2, 1 kDa. Freeze-drying of the composition comprising exosomes, trehalose and LMW HA allows for storage at room temperature without significant loss of the exosomes' structural and functional integrity. According to an embodiment, the freeze-dried composition comprising the exosomes, trehalose and LMW HA as described herein, can be stored at room temperature for at least 3 months, at least 6 months, at least 9 months, at least 12 months or 1 year, or, at least 18 months or 1.5 years. As demonstrated in the examples herein, exosome concentration upon storage for up to 6 months of the freeze-dried composition at room temperature shows very little variability at different temperatures and exosome concentration is at least 75%, at least 80%, at least 85%, or at least 90% of the starting concentration. A combined use of lower than 10 kDa molecular weight hyaluronic acid and trehalose in cryoprotection of plant exosomes results in higher exosome concentration and better morphology in lyophilization. Also, the combination of trehalose and LMW HA with molecular weight lower than 10 kDa while preventing aggregation during lyophilization, resulted in a smaller, homogenous, and higher concentration of exosomes.

Hyaluronic acid (HA), also called hyaluronan, is a natural non-toxic, anionic, non-sulfated glycosaminoglycan. In vivo, it is distributed widely throughout connective, epithelial and neural tissue. Depending on the size of the hyaluronic acid molecule, it shows different physical and biological properties.

Currently, there is no uniform consensus on the division of HA in terms of the molecular size. For the purpose of the present invention, "low molecular weight HA" ("LMW HA") has a molecular weight (Mw) below 200 kDa. The Mw of HA is defined to be the weight-average Mw of HA used, which can be measured using light scattering techniques known in the art, in particular multi-angle light scattering (MALS). According to an embodiment, the LMW HA used for the cryoprotectant described herein is oligo HA having a Mw below 20 kDa. According to a further embodiment, the LMW HA is oligo HA having a Mw below 10 kDa.

According to an embodiment, the weight-to-weight ratio of trehalose to LMW HA in the cryoprotectant or freeze-dried composition may vary e.g. between 0.2 and 50. According to another embodiment, the ratio is at least 0.4, 0.5, 0.6 or 0.7 and/or, at most 5, 3, 2, 1.5, 1.2, 1, or 0.9, or, about 0.8.

The concentration of LMW HA in the composition comprising exosomes, trehalose and LMW HA prior to freeze-drying is between 0.1 and 5% w/w. According to an embodiment, the concentration of LMW HA in the composition comprising exosomes, trehalose and LMW HA prior for freeze-drying is at least 1.0%, at least 2.0%, at least 2.1%, at least 2.2%, at least 2.3%, or about 2.5%, and/or at most 5%, at most 4.8%, at most 4.6%, at most 4.5%, at most 4.3%, at most 4.0%, at most 3.7%, at most 3.5%, at most 3.3% or at most 3%.

The concentration of trehalose in the composition comprising exosomes, trehalose and LMW HA prior to freeze-drying is between 1 and 5%. According to an embodiment, the concentration of trehalose in the composition comprising exosomes, trehalose and LMW HA prior for freeze-drying is at least 25 mM, at least 30 mM, at least 35 mM, at least 40 mM, at least 45 mM, or, about 50 mM, or, at most 100 mM, at most 90 mM, at most 80 mM, at most 70 mM, at most 65 mM, at most 60 mM or at most 55 mM.

According to an embodiment, the ratio of EVs, in particular exosomes, to cryoprotectant is 1:3 to 3:1, 1:3 to 1:1, or, 1:3 to 1:2. In one embodiment, the ratio is 1:3 to 1:2.

According to a further embodiment, the cryoprotectant consists essentially of the combination of trehalose and LMW HA as described herein, i.e. no further excipients are required to obtain the advantageous protective effect for the purpose of longer term storage of the freeze-dried composition comprising exosomes at ambient temperature and ultimately safeguarding the functionality of the resulting exosome composition. E.g. the freeze-dried composition does not require the presence of, or, does not comprise, methionine and/or mannitol or any other further polyol typically used as cryoprotectant. Consequently, in an embodiment, a freeze dried composition comprising exosomes and the cryoprotectant consisting essentially of the combination of trehalose and LMW HA is provided. According to another embodiment, the cryoprotectant is essentially free of dimethylsulphoxide (DMSO). Alternatively, DMSO is not added to the cryoprotectant.

"Extracellular vesicles" (EVs) are lipid bilayer-delimited particles that are naturally released from almost all types of cells and, unlike a cell, cannot replicate. EVs are according to size and synthesis route divided into exosomes (30-200 nm), microvesicles (100-500 nm) and apoptotic bodies (500 nm-2 pm). They carry a cargo of proteins, nucleic acids, lipids, metabolites, and even organelles from the parent cell. A wide variety of EV subtypes have been proposed, defined variously by size, biogenesis pathway, cargo, cellular source, and function, leading to a historically heterogenous nomenclature.

As used herein, "exosome" refers to a class of extracellular vesicles of endosomal origin through the fusion and exocytosis of multivesicular bodies into the extracellular space. Exosomes are typically the smallest type of extracellular vesicle having 30-200 nm in diameter. Enveloped by a phospholipid bilayer, exosomes are released into the extracellular environment containing a complex cargo of contents derived from the original cell, including proteins, lipids, mRNA, miRNA and DNA.

"Microvesicles" bud directly from the plasma membrane, have a 100-500 nm size and include cytoplasmic material. They are formed via the direct outward blebbing and pinching of the plasma membrane releasing the nascent microvesicle into the extracellular space and as a consequence contain various levels of cell membrane bound molecules.

"Apoptotic bodies" are 500 nm-2 ∞m vesicles typically released from apoptosis mediated dying cells. Apoptosis progresses through several stages, first nuclear chromatin condensation, then nuclear splitting and the frequent appearance of micronuclei, then membrane blebbing, and finally, splitting of the cellular content into distinct membrane-enclosed vesicles, termed apoptotic bodies. While microvesicles and exosomes appear to operate as 'safe containers' mediating intercellular communication of live cells, apoptotic bodies appear after the disassembly of an apoptotic cell into subcellular fragments.

According to an embodiment, the EVs, and in particular exosomes, are derived from plant material, in particular edible plant material. Plant derived exosomes are also referred to as PDEs. The plant source will determine specific properties and therefore potential use of the EVs, in particular exosomes. In an embodiment, the exosomes are PDEs from a plant selected from cloudberry, grape, grapefruit, strawberry, raspberry, blueberry, apple, cucumber, tomato, olive, celery, lemon, ginger or soy. In one embodiment, plant material considered for the purpose of the present disclosure includes specific parts of a plant such as leaves and/or stem, stalks (e.g. celery), root (e.g. ginger root), or fruit (e.g. grape, grapefruit, lemon (in particular lemon peel), strawberry, raspberry, blueberry, apple, cucumber, tomato or olive) of the plant, in particular cloudberry, grape, strawberry, raspberry, blueberry, apple, cucumber, tomato, olive, celery and ginger, more in particular, cloudberry, grape, cucumber, soy, olive, and ginger. In an alternative embodiment, EVs, and in particular exosomes, are obtained from plant derived cells in culture formed in a controlled environment in vitro, e.g. callus. Upon callus formation, plant cells dedifferentiate to reach a stem cell like status. Callus tissue provides a cost-effective, environmentally friendly, and sustainable source of natural ingredients which could benefit skin cells.

In some embodiments of the present disclosure, the cryoprotectant, freeze-dried composition or production process exosomes are PDEs from cloudberry callus. Cosmetic compositions containing cloudberry (Rubus chamaemorus) cell culture preparation, i.e. cloudberry callus, promotes antioxidant activity, anti-aging effect, procollagen I synthesis and protects human skin cells from UV radiation effects. In a further embodiment, EVs, and in particular exosomes, are obtained from cloudberry callus.

According to a further embodiment, the freeze-dried exosome composition as described herein is essentially free of apoptotic bodies. For the purpose of the present invention, the exosomes are separated from apoptotic bodies that may also be present in the source material from which the exosomes are derived, typically using size-exclusion technique, in particular ultrafiltration using a membrane with a cut-off of at most 100 kDa. Accordingly, in an embodiment, the exosome composition contains a fraction of EVs containing (or consisting essentially of) the combination of exosomes and microvesicles.

According to an embodiment, the plant derived EVs, in particular exosomes, are provided in a plant derived exosome containing liquid for further manipulation or method steps as described herein. The plant derived exosomes are obtained from the plant material by an exosome isolation method including at least the steps of:

homogenisation of the plant material thereby providing a (liquid) homogenised plant cell preparation, and, subjecting the plant cell preparation to a filtration process comprising at least one ultrafiltration step using a filter membrane having a cut-off smaller than or equal to 100 kDa, thus obtaining the exosome containing liquid.

In a preferred embodiment, the exosome containing liquid is provided by a method comprising the steps:

providing a homogenised plant cell preparation containing the PDEs, and, subjecting the plant cell preparation to a filtration process comprising at least one ultrafiltration step using a filter membrane having a cut-off smaller than or equal to 10 kDa.

Homogenisation of the plant material can be achieved using ordinary methods known in the art including techniques such as mechanical chopping, grinding and/or juicing the plant material. Pre-treatment of the plant material, e.g. by soaking or macerating the plant material, e.g. to make it softer, can facilitate the homogenisation of the plant tissue.

In one embodiment of the present disclosure, freeze-dried composition or production process according to any of the preceding claims, wherein the exosomes are PDEs isolated from plant juice or plant callus tissue.

According to an embodiment, the homogenised plant cell material is juice, in particular in case the plant material is the fruit or root of the concerned plant. As used herein, "juice" thus refers to the natural fluid, fluid content, or liquid part that can be extracted from a plant or one of its parts. A juicer can be used to obtain homogenised plant cell preparation (or otherwise) applying shear force to disintegrate the plant material and obtain the plant juice to be used as homogenised plant cell preparation. To facilitate the juicing process, water or phosphate buffered saline (PBS) can be added to the plant material in the juicer.

According to an embodiment, in case the plant material is callus tissue, in particular callus tissue grown in vitro, the homogenised plant cell preparation is obtained by mixing the callus tissue in water, PBS or growth medium wherein the callus was grown. Mixing can be achieved by gently shaking the recipient (e.g. flask, erlenmeyer, petri dish) containing the callus tissue, and, water, PBS or growth medium, at about 120 rpm, or, at 100-150 rpm, at 100-175 rpm, at 100-200 rpm, or 100-300 rpm.

According to an embodiment, an ultrafiltration membrane used has a cut-off smaller than or equal to 3 kDa, 5 kDa, 10 kDa, 30 kDa or 100 kDa. Samples obtained using a membrane with a smaller cut-off contain an EV fraction with a relatively higher content of exosomes and are preferred for use in the skin product described herein. Accordingly, in a particular embodiment, the membrane has a cut-off of about 10 kDa or smaller. According to a further embodiment, the ultrafiltration membrane is a cellulose membrane with the 3, 5, 10, 30 or 100 kDa cut off which allows fast and easy isolation of EVs of interest, in particular exosomes. In particular, the ultrafiltration membrane is a cellulose membrane with a 3, 5 or 10 kDa cut-off.

In accordance with the methods described herein, ultrafiltration is typically done by centrifugal filtration at 3000×g or more, preferably 4000×g, for at least 30 minutes, at least 40 minutes, at least 50 minutes, at least 60 minutes, and/or, at most 120 minutes, at most 90 minutes or at most 60 minutes. Alternative ultrafiltration methods can be used provided an ultrafiltration membrane having the required characteristics as defined herein is used. Equally, alternative size exclusion based separation techniques can be used such as tangential flow filtration and size-exclusion chromatography. In particular isolation techniques that provide for a preparation containing the exosomes while excluding apoptotic bodies (to the extent feasible) are envisaged for the purpose of the present disclosure.

According to a further embodiment, the isolation method for obtaining the plant derived exosome containing liquid by ultrafiltration further comprises prior to the ultrafiltration step one or more of the steps:

(1) filtering the homogenised plant cell preparation through a juice filter net and retaining resulting liquid, (2) centrifugation of the homogenised plant cell preparation or resulting liquid at least 400×g for at least 10 minutes and retaining the supernatant, and/or, (3) filtering the homogenised plant cell preparation, the supernatant or resulting liquid through a membrane filter, e.g. with a pore size of about 0.2 μm.

EVs, in particular exosomes, are an effective and safe delivery vehicle with high biocompatibility, strong cargo loading and releasing ability which can cross biological barriers and facilitate targeted drug delivery. According to an embodiment, the exosomes for inclusion in the freeze-dried compositions described herein can be loaded with (a) further active ingredient(s). Consequently, the EVs, in particular exosomes, are used as carriers for the active ingredient to the deeper layers of the epidermis. In a further embodiment, said active ingredient is selected from natural compounds such as β-Elemene, Celastrol, Doxorubicin, Paclitaxel, picroliv, Arnebin-1 and hydrophobic therapeutic compounds such as Curcuma, single or a combination of skin peptides and vitamins, in particular from the hydrophobic therapeutic compounds. In a specific embodiment, the exosomes are loaded with an active ingredient, such as Curcuma.

According to a further embodiment, a production process for the freeze dried composition comprising exosomes, in particular PDEs, trehalose and LMW HA is provided, comprising the steps of:

(a) providing the exosomes in a water based liquid preparation, (b) combining the exosomes with the cryoprotectant comprising trehalose and LMW HA as described herein, to obtain a water based preparation combining the exosomes and cryoprotectant, and, (c) freeze drying the combined exosome cryoprotectant preparation.

According to an embodiment, step (a) is performed according to the exosome isolation method for plant derived exosomes described herein.

According to an embodiment, the preparation combining the exosomes and cryoprotectant as obtained in step (b) comprises trehalose and LMW HA in a weight-to-weight ratio of trehalose to LMW HA of at least 0.4, 0.5, 0.6 or 0.7 and/or, at most 5, 3, 2, 1.5, 1.2, 1, or 0.9, or, about 0.8. According to another embodiment, the concentration of LMW HA in the composition comprising exosomes, trehalose and LMW HA as obtained in step (b) is at least 1.0%, at least 2.0%, at least 2.1%, at least 2.2%, at least 2.3%, or about 2.5%, and/or at most 5%, at most 4.8%, at most 4.6%, at most 4.5%, at most 4.3%, at most 4.0%, at most 3.7%, at most 3.5%, at most 3.3% or at most 3%. According to another embodiment, the concentration of trehalose in the composition comprising exosomes, trehalose and LMW HA as obtained in step (b) is at least 30 mM, at least 35 mM, at least 40 mM, at least 45 mM, or, about 50 mM, or, at most 100 mM, at most 90 mM, at most 80 mM, at most 70 mM, at most 65 mM, at most 60 mM or at most 55 mM.

According to an embodiment, step (c) is performed by lyophilisation, comprising the steps of freezing the preparation obtained in step (b), subjecting the frozen preparation to reduced pressure for drying. Freezing of the preparation can be done at a temperature below −30° C., −50° C., −60° C., −70° C., or −80° C. The freezing can take at least 6 hours, 8 hours, at least 10 hours, at least 20 hours, or at least 30 hours. Pressure during drying is reduced to below 0.5 mbar or lower, 0.1 mbar or lower, 0.05 mbar or lower. Samples are maintained at reduced temperature below −20° C. or −30° C. when subjected to reduced pressure for drying. Alternative cryodesiccation technologies are equally considered such as spray-drying.

In one embodiment of the present disclosure, the freeze-dried composition is for use in a skincare product. The freeze-dried composition as described herein, in particular comprising PDEs, is useful as a component of a skincare product. As used herein, a “skincare product” is a product for application to the skin typically to maintain or improve skin structure and/or appearance. Specific purpose for the skincare product described herein is for example wound healing, scar minimisation, overall improvements in skin appearance such as wrinkle correction, brightening of the skin or firming of the skin. As demonstrated in the examples, the exosome preparations, in particular the plant based exosome preparations, described herein exhibit favourable effect on human dermal fibroblast’s activity thereby supporting restorative action on the skin in structure and appearance. In a further embodiment, a skincare product is provided comprising freeze-dried composition containing callus derived exosomes, in particular cloudberry callus derived exosomes, more in particular curcumin loaded cloudberry callus derived exosomes. Alternatively, a skincare product is provided comprising a freeze-dried composition containing apple derived exosomes, in particular curcumin loaded apple derived exosomes.

In an embodiment, compositions described herein, i.e. comprising the exosomes, trehalose and LMW HA, have a pH ranging from acidic to neutral, such as from 2.5 to 7.5, or, at least 2.5, at least 3, at least 3.5, and/or, at most 7.5, at most 7, at most 6.5, or at most 6. In a further embodiment, pH of the composition is between 3 and 4, or, about 3.5.

In one embodiment, the freeze-dried composition is applied to the skin using a dermatologically acceptable liquid excipient. Another embodiment relates to a method for applying the freeze-dried composition to the skin comprising the step of mixing the freeze-dried composition with a liquid excipient prior to application to the skin. For said purpose, the liquid excipient is a dermatologically acceptable excipient. According to a further embodiment, the mixing occurs just prior to application of the skin product to the skin, e.g. by using means for mixing in the device for dispensing the liquid excipient and freeze-dried composition from the respective containers in the device (otherwise separating the liquid and the freeze-dried composition) for immediate application to the skin. The liquid excipient can be any dermatologically acceptable liquid including an aqueous liquid, an oil, a lotion, an oil-in-water (o/w) or water-in-oil (w/o) emulsion, or a suspension. In particular water-based excipients are used, such as an aqueous liquid, water based lotion or o/w emulsion.

According to an embodiment, the liquid excipient may comprise further components, in particular a skin penetration enhancer. The skin penetration enhancer can be selected from terpenes such as essential oils, fatty acids containing 1,8-cineole, d-limonene, and l-menthol such as squalene, niaouli, eucalyptus, Alpinia oxyphylla, turpentine, sweet basil and tulsi, cardamom, peppermint, fennel, black cumin and fish oil, polysaccharides, acids, alcohols, fatty alcohols, amines, esters, surfactants and vitamins such as C and retinol. According to a further embodiment, the skin penetration enhancer is vitamin C or retinol. In an embodiment of the present disclosure, the liquid excipient further comprises a skin penetration enhancer selected from terpenes, and fatty acids containing 1,8-cineole, d-limonene, and l-menthol such as squalene, niaouli, eucalyptus, Alpinia oxyphylla, turpentine, sweet basil and tulsi, cardamom, peppermint, fennel, black cumin, fish oil, as well as polysaccharides, acids and vitamins.

Further methods for increased delivery of the exosome preparations disclosed herein include mechanical skin delivery methods such as microneedles, e.g. marine sponge spicules, or polymeric and biological networks such as hydrogels. Enhanced delivery methods can also be combined for optimal delivery.

The cryoprotectant described herein allows for storage of the exosomes for an extended time at room temperature, thus allowing the exosome material to be distributed and stored at ambient temperature up to the moment of application to the skin. In an embodiment, the freeze-dried composition is administered to the skin by means of a two-compartment dispensing device containing the freeze-dried composition in one compartment and the liquid excipient in a second compartment, and, wherein the freeze-dried composition is mixed with the liquid excipient upon dispensing the skincare product to the skin. According to an embodiment, a two-compartment dispensing device is used to keep the freeze-dried composition separated from the liquid excipient during distribution and storage of the skincare product. The device is designed to mix the appropriate dose of freeze-dried product with the appropriate amount of liquid excipient when dispensing the product and applying to the skin. Typically, the dispensing mechanism is a pump taking a predefined amount of material from both compartments when operated to dispense the product.

Experimental Part

Statistical analyses were performed using Student's t-test or ANOVA as appropriate and the results were considered significant when $p<0.05$.

Example 1

Plant Cell Suspension Preparation

Plant cells from which exosomes are isolated were obtained from two sources: 1) plant callus obtained by plant tissue culture, namely cloudberry callus (Rubus chamaemorus), and, 2) plant juice from edible fruits, roots, and peels including grape, grapefruit, ginger, strawberry, raspberry, blueberry, apple, cucumber, tomato, olive, celery, lemon peel, and soymilk.

Cloudberry callus formation: cloudberry leaves, stems and flowers were collected at the end of June, sterilized in 70% ethanol for 2 min, followed by 10 min in 2% hypochlorite containing a few drops of Tween 20. The leaves dried and cut into 1 $cm^2$ sections. Plant sections were transferred to petri dishes containing the solid Murashige and Skoog (MS) media containing 30 g/L sucrose, 8 g/L Bacto agar, 0.1 mg/L kinetin, and 1 mg/L $\alpha$-naphthaleneacetic acid (based on protocol described by Murashige, T., Skoog, F. Physiol. Plant 1962, 15, 473-497). The petri dishes with cloudberry sections were sealed with parafilm and incubated at 23° C. under a day-night illumination regime (photoperiod 16:8 h; irradiation 40 μmol m−2s−1). Soft yellow calli formed after 15 to 20 months. 100-200 mg of fresh yellow callus was transferred into 50 mL Erlenmeyer flask containing 15 mL media without agar and incubated for 10 days in a shaker incubator at 120 rpm at 23° C. to obtain a callus cell suspension.

Plant juice from edible fruits, roots, and peels was obtained from the different plant sources using a juice maker. For root plants including ginger, fresh cold PBS was added to the juice maker.

Example 2

Exosome Isolation

Exosomes were isolated by ultrafiltration. Ultracentrifugation was used for comparison. For both methods, the callus suspension and plant juices were passed through a juice filter net to obtain a homogenous cell suspension.

For the ultrafiltration method, the homogenous cell suspension was centrifuged at 400×g for 10 minutes. The supernatant was then transferred to a new tube and centrifuged at 1,500×g for 20 minutes. The supernatant was then passed through a 0.2 μm membrane filter to remove cell debris and bigger parts. The filtrate was then subjected to ultrafiltration using Centricon® Plus-70 Centrifugal Filter, with 10 kDa cutoff, and, centrifuged at 4,000×g centrifugation for 20 minutes. The filtrate supernatant containing the exosomes is stored at −80° C. for further experiments.

For ultracentrifugation, plant extracts such as juice and callus suspension were centrifuged at 300×g for 10 min to remove debris. The supernatant is then centrifuged at 2000×g for 20 min followed by transferring the supernatant to a sterile Ultra-Clear tube (Beckman Coulter, Sharon Hill, PA, USA) and centrifugation in a Beckman Coulter OptimaT™ L-80XP Ultracentrifuge to isolate exosomes by 40 min centrifugation at 10,000×g. After this, the supernatant was again collected and centrifuged at 100,000×g for 90 min to pellet exosomes. The resulting exosome pellet was resuspended in 1×PBS or deionized water and stored at −80° C. for future use. All procedures are performed at 4° C.

Example 3

Exosome Characterization

The protein concentration of isolated exosomes is measured by BCA protein assay kit. Isolated exosomes were characterized by fluorescent staining, Transmission electron microscopy (TEM), and Nanoparticle Tracking Analysis (NTA).

3.1 TEM

For TEM imaging, exosomes are fixed with 4.0% paraformaldehyde (PFA) in sodiumphosphate buffer and stained with 2% neutral uranyl acetate with embedding in uranyl acetate and methylcellulose mixture. Exosomes are viewed with transmission EM using Jeol JEM-1400 (Jeol Ltd., Tokyo, Japan) operating at 80 kV. Images are taken with Gatan Orius SC 1000B CCD-camera (Gatan Inc., USA) with 4008×2672 px image size and no binning.

3.2 NTA

Particle number and size distribution of the exosome is measured by NTA instrument LM14C (NanoSight LTD., London, UK) equipped with blue (404 nm, 70 mW) laser and sCMOS camera. Data are analysed with Nanosight software v3.0, using threshold 5 and gain 10.

Example 4

Isolation and Characterisation of Apple Exosomes

Exosomes were isolated from 200 mL of apple juice by ultrafiltration and ultracentrifugation methods as specified in example 2. The morphology of isolated plant exosomes was characterized by TEM (see protocol 3.1). Both methods result in round shape exosomes (see FIG. 2 (*a*)). Particle number and size distribution of isolated exosomes were measured by the NTA instrument (see protocol 3.2). The results (see FIG. 2 (*b*) & (*d*)) showed that while exosomes isolated by both methods resulted in particles with diameters ranging between 30 to 300 nm, exosomes isolated by ultrafiltration showed smaller particle size by almost 30% with an average diameter of 162 nm compare to exosomes isolated by ultracentrifugation with an average diameter of 230 nm. Furthermore, the results (see FIG. 2 (*b*) & (*c*)) showed that ultrafiltration results in a higher particle numbers compare to ultracentrifugation by approximately 45%. Moreover, data from a wound scratch assay (see 7.1) showed that treatment of human dermal fibroblasts with isolated exosomes using ultrafiltration accelerates wound healing faster than exosomes isolated by ultracentrifugation almost by 13% (see FIG. 2 (*e*)). These data may indicate the potential mechanical damage to the exosomes during ultracentrifugation due to the high-speed centrifugation which leads to protein aggregation, lower concentration, and bigger exosomes size.

Example 5

Protocol for Exosome Loading with an Active Substance

Exosome loading with active substances was achieved using the freeze-thaw methodology. By way of example, the protocol for preparing curcumin loaded plant exosome (Cu-Exo) is provided as well as its characterization.

Plant exosome preparation as obtained in example 2 was brought to room temperature. Curcumin first is diluted in DMSO and then is mixed with the plant exosome in a fixed proportion of 1:4 W/W exosome to curcumin. Typically, an exosome preparation obtained by ultrafiltration as described above containing $10^{10}$-$10^{12}$ exosome particles per ml corresponds to about 1 mg/ml. The mixture was incubated for 15 min at room temperature and then transferred to −80° C. This freeze-thawing procedure was repeated three times. Free curcumin was removed by centrifuging the preparation twice at 5,000×g. The final solution was precipitated either using a total exosome isolation reagent (ThermoFisher Scientific, Grand Island, NY, USA) or centrifugation at 100000×g for 3 hours. The in vitro concentration of curcumin before and after encapsulation into the exosomes was measured using a Nanodrop 1000 spectrophotometer at 420 nm. Briefly, same concentration of curcumin and exosome-loaded curcumin was added to PBS and incubated at 37° C. in dark over 3 hours. The stability of curcumin was measured using spectrophotometer at 420 nm wavelength over 180 minutes. The results showed that encapsulation of curcumin into the exosomes increased curcumin's stability by 70% (see FIG. 3 (*a*)). Furthermore, in the scratch wound assay (see 7.1) plant exosomes encapsulated curcumin accelerated the healing time and cell proliferation the most compared to non-treated human dermal fibroblasts (control) by almost 37% and 46%, respectively. Data also showed that encapsulated curcumin accelerated wound healing and cell proliferation by 28% and 14% respectively when compared to free curcumin (see FIG. 3 (*b*)-(*e*)).

Example 6

Plant Exosome Preservation 6.1 Testing of Different Cryoprotectants

Different cryoprotectant components namely trehalose, mannitol, sorbitol, sucrose, glucose and HA (both low Mw (LW) and high Mw (HMW)), either alone or in combination with HA or glycine (see Table 1) were tested for exosome viability outcome after lyophilization. PBS (290 mOsm/kg) was used as the solvent. The LMW HA used for the examples described herein is LMW HA having a Mw lower than 10 kDa. Isolated exosomes (1 mg/ml) were dissolved in PBS solution and then mixed with cryoprotectant solution in the ratio of 1 part exosomes to 1, 3, 5, or 10 parts of cryoprotectant.

TABLE 1 cryoprotectants used including the components and concentration in the cryoprotectant solution.

| Cryoprotectant | Component 1 | % w/v | Component 2 | % w/v |
|---|---|---|---|---|
| 1 | Hyaluronic acid (HMW) | 4 | | |
| 2 | Hyaluronic acid (LMW) | 4 | | |
| 3 | Trehalose | 4 | | |
| 4 | Mannitol | 4 | | |
| 5 | Sorbitol | 4 | | |
| 6 | Sucrose | 4 | | |
| 7 | Glucose | 4 | | |
| 8 | Trehalose | 2 | HMW HA | 2.5 |
| 9 | Trehalose | 2 | LMW HA | 2.5 |
| 10 | Trehalose | 2 | Glycine | 0.2 |

TABLE 1-continued cryoprotectants used including the components and concentration in the cryoprotectant solution.

| Cryoprotectant | Component 1 | % w/v | Component 2 | % w/v |
|---|---|---|---|---|
| 11 | Mannitol | 2 | LMW HA | 2.5 |
| 12 | Sorbitol | 2 | LMW HA | 2.5 |
| 13 | Sucrose | 2 | LMW HA | 2.5 |
| 14 | Glucose | 2 | LMW HA | 2.5 |

Cryoprotectant solutions were prepared using phosphate-buffered saline (PBS) while the overall osmolality of the lyophilization solutions was maintained at 290 mOsm/kg. Isolated exosomes ($10^{10}$-$10^{11}$ particle/ml) were suspended in cryoprotectant solution ranging from 1 part of exosome suspension with 3 parts of cryoprotectant solution, to, 3 parts of exosome suspension with 1 part of cryoprotectant solution. Exosomes were lyophilized and then morphology of retrieved exosomes was visualized by TEM while size and concentration were measured by NTA (see FIG. 4). Overall lyophilization using any cryoprotectant tested, resulted in an improvement of exosome viability or integrity. The results showed that cryoprotectants prevented the aggregation of exosomes during lyophilization significantly. However, a combination of trehalose with low molecular weight HA displayed higher exosome concentration and better morphology (not aggregated or damaged) than the other cryoprotectants tested. Combinations of trehalose and low molecular weight HA were therefore further explored.

6.2 Freeze-Drying Exosomes Using Trehalose, Hyaluronic Acid and Combinations Thereof To test the preservation of exosome functionality and integrity during the lyophilization process, two cryoprotectants (trehalose and LMW HA) in four different cryoprotectant combinations were used, namely: 50 mM trehalose, 100 mM trehalose, 5% LMW HA, and 50 mM trehalose +2.5% LMW HA. Lyophilization solutions were prepared using PBS. The overall osmolality of the lyophilization solutions was maintained at 290 mOsm/kg. For the freeze-drying experiments, isolated exosomes ($10^{10}$-$10^{11}$ particle/ml) were suspended in cryoprotectant solution. 5 ml of each sample was prepared. Each solution was divided into 3 polypropylene microcentrifuge tubes, each tube containing 1.2 ml of lyophilization solution supplied with exosomes. Samples were stored overnight at −80° C. degrees. Samples were loaded into the freeze dryer (Epsilon 2-16D LSCplus freeze dryer, Germany). Samples were lyophilized for 24 h at an environmental temperature conditioned to 22° C., operating temperature lower than −30° C., and at pressure of <0.05 mbar. Final product was stored for further analysis at −80° C. in a tightly sealed box to prevent moisture absorption and light exposure.

Exosomes obtained from apples using the ultrafiltration protocol of example 2 were freeze-dried as described, rehydrated (see 8.4 to obtain rehydrated lyophilised exosomes), and characterized by TEM and NTA. TEM images (FIG. 5 (*a*)) show that there is no exosome aggregation when using trehalose. Also, NTA results (FIG. 5 (*b*)) showed that the combination of trehalose and LMW HA while preventing aggregation during lyophilization, resulted in a smaller, homogenous, and higher concentration of exosomes compared to LMW HA and trehalose alone. FIG. 5 (*c*) and (*d*) show that size and concentration of lyophilized exosomes compared to the non-lyophilized control sample are not affected by the freeze-drying process when the combination of trehalose and LMW HA is used as cryoprotectant.

6.3 Effect of Freeze Drying on Exosome Concentration after Storage at Different Temperatures The concentration of lyophilized and non-lyophilized exosomes was measured by BCA kit at 0 h, 1 month, 3 months, and 6 months after lyophilization and isolation, −20° C. (FIG. 7(*a*)), +4° C. (FIG. 7(*b*)) and room temperature (FIG. 7(*c*)). Lyophilized exosomes were rehydrated before performing the experiment (see 8.4 to obtain rehydrated lyophilised exosomes). Both lyophilized and non-lyophilized exosomes were kept in −20° C., +4° C. and room temperature for a certain time before their concentration was measured. Data show that the concentration of non-lyophilized exosomes significantly dropped over time while the concentration of lyophilized exosomes is stable over time when stored at ranging temperatures.

Example 7

Exosomes Retention of Activity and Functionality Assay

The biological activity of exosome preparations can be measured is assessed by a wound scratch and MTT assay.

7.1 Wound Scratch Assay.

Human dermal fibroblasts are seeded in 96 well plates at $2.4\times10^4$ cells/well. A cell-free area is then created in a confluent monolayer by physical exclusion through mechanical damage using a 10 ml pipette tip. The culture medium is replaced immediately with a fresh 0.5% EV-free serum-supplemented culture medium containing 100 μg/ml of each exosome preparation tested. Three positions per scratch are imaged for 48 hours. Relative wound density is analysed by measuring the wound area over the healing time. All scratch assays are performed in triplicate.

7.2 MTT Assay.

The effect of the exosomes on the proliferation of human dermal fibroblasts was measured by a 3-[4.5-Dimethylthiazol-2-yl]-2.5-diphenyltetrazolium bromide (MU; Life technologies) assay. Briefly, human dermal fibroblast cells are seeded in 96-well plates at an initial density of $5\times10^3$ cells/well for 24 h and then are treated with 100 μg/mL of exosomes for 48 hours. Cells are incubated with 0.5 mg/mL of MTT for 3-5 h and then 100 μl DMSO is added to each well and the optical density is measured at 540 nm.

Example 8

Wound Healing Effect of Plant-Derived Exosome Compositions 8.1 Exosomes Isolated from Varying Plant Sources Exosomes were isolated from 14 different plant sources namely cloudberry callus, cloudberry juice, grape juice, grapefruit juice, strawberry juice, raspberry juice, blueberry juice, apple juice, cucumber juice, tomato juice, olive juice, celery juice, lemon peel, ginger rhizome and soymilk. The results of the wound scratch assay as illustrated in FIG. 1 show that exosomes extracted from edible fruits, except lemon peel and grapefruit significantly accelerate wound closure after 50 h. Data also show that exosomes isolated from cultured cloudberry callus promote wound healing the most.

8.2 Exosomes Isolated by Ultrafiltration Versus Ultracentrifugation

Wound scratch assay was performed using the apple exosomes isolated either by ultrafiltration or ultracentrifugation as described in example 4. Results are shown in FIG. 2 (*e*).

8.3 Curcumin Loaded Exosomes

Wound scratch assay (see 7.1) was performed using curcumin, apple exosomes, and curcumin-loaded apple exosomes, and relative wound density was measured at 24 hours. Plain medium and DMSO were used as negative and positive controls respectively. The results as illustrated by FIG. 3 show that curcumin-loaded plant exosomes promote wound healing faster than either curcumin or plant exosomes alone. This data shows plant exosomes present an efficient delivery system to increase bioavailability and enhance the delivery of active substances such as curcumin to human cells, human dermal fibroblasts in particular.

In a second assay, human dermal fibroblasts were incubated with curcumin, apple exosomes, and curcumin-loaded apple exosomes for 24 hours. Plain medium and DMSO are used as negative and positive controls respectively. Then, the proliferation rate was measured using the MU assay (see 7.2). The results shown in FIG. 3(*e*) illustrate that curcumin-loaded apple exosomes promote fibroblasts proliferation compared to other samples. The data show that plant exosomes can efficiently deliver active ingredients to the target cells while preserving the cell's functionality.

28.4 Lyophilised Versus Non-Lyophilised Exosomes

Figure 6:
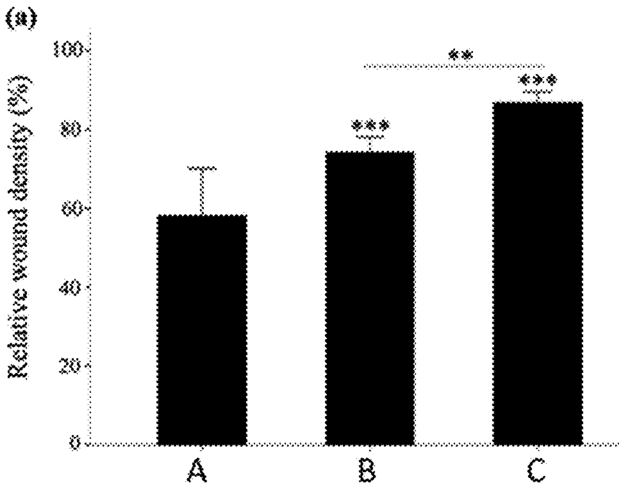
FIG. 6 illustrates the effect of lyophilized exosomes containing cryoprotectants including trehalose and LMW HA on fibroblasts' activity (A: control; B: rehydrated lyophilized exosomes; C: reconstituted lyophilized exosomes): (a) Relative wound density of human dermal fibroblasts, (b) Fibroblasts' proliferation measurement by MTT colorimetric assay, and (c) collagen production by fibroblasts incubated with exosomes for 48 h, as described in example 8.4.
Figure 6:
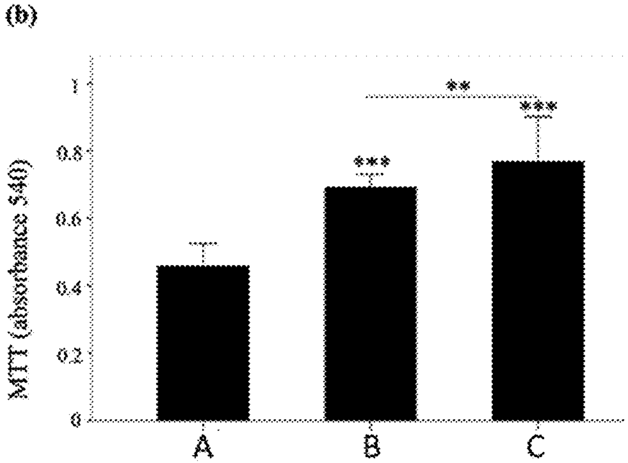
Figure 6:
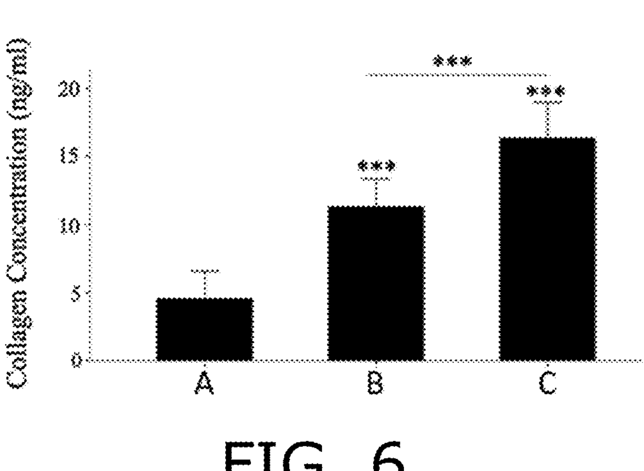

The effect of lyophilisation on exosomes activity was measured for non-lyophilised exosomes (control), rehydrated lyophilised exosomes and reconstituted lyophilised exosomes. Rehydrated lyophilized exosomes are obtained from lyophilised exosomes which were transferred to 4° C. for 1 hour and then rehydrated to remove trehalose and/or HA by diafiltration using the Amicon filtration system with 1×PBS adding the original volume of 1×PBS thereby removing cryoprotectant from the liquid phase. Samples containing reconstituted lyophilised exosomes were not subjected to further treatment following reconstitution of the lyopilised material with 1×PBS. Human dermal fibroblasts were incubated with the exosome samples for 24 hours. Wound scratch assay (protocol see example 7; FIG. 6 (*a*)) and MU assay (protocol see example 7; FIG. 6 (*b*)) show an advantageous effect of both the presence of the cryoprotectant as well as the freeze-drying on the functionality of the exosomal preparation.

Also, collagen production was measured using a human collagen type I ELIZA kit. Human dermal fibroblasts were incubated with the exosome samples for 48 h. 100 μl of cell culture media was collected from each sample and incubated with 100 μl of biotinylated detection antibody for 1 h at 37° C. Samples were then washed and incubated with 100 μl of horseradish peroxidase (HRP) conjugate working solution. Stop solution was added and optical density was measured at 450 nm with a Plate Reader. The experiment also shows an advantageous effect of both the presence of the cryoprotectant as well as the freeze-drying using the cryoprotectant on the functionality of the exosomal preparation (see FIG. 6(*c*)).

Example 9

Effect of pH

Figure 8:
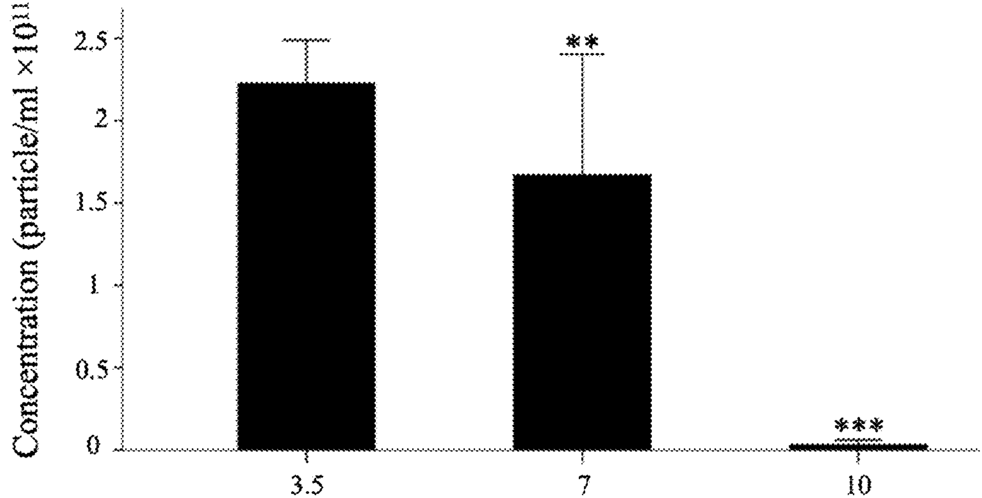
FIG. 8 illustrates exosome stability at different pH by measuring the exosome concentration after 2 hours at the indicated pH.

FIG. 8 shows the effect of the pH on the freeze-dried exosomes following rehydration of the freeze-dried exosomes.

Example 10

Packaging for Cosmetic Use

Figure 9:
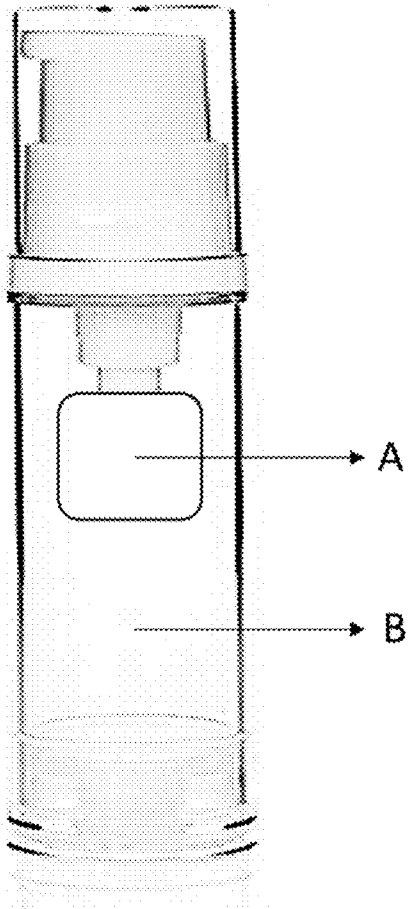
FIG. 9 provides a schematic design of a packaging device for a skincare formulation containing exosomes wherein a freeze-dried powder containing exosomes is located in a powder compartment while the liquid of the formulation was located in a water compartment.

Lyophilized powder containing exosomes is formulated for different skin improvement purposes as skincare products, convenient for domestic use. For the packaging, a packaging device with at least two separated compartments, such as the liquid powder mixing airless bottle as illustrated in FIG. 9, is used wherein the freeze-dried powder containing exosomes is located in a powder compartment while the liquid of the formulation is located in a water compartment.

DETAILED DESCRIPTION OF THE DRAWINGS

Figure 1B:
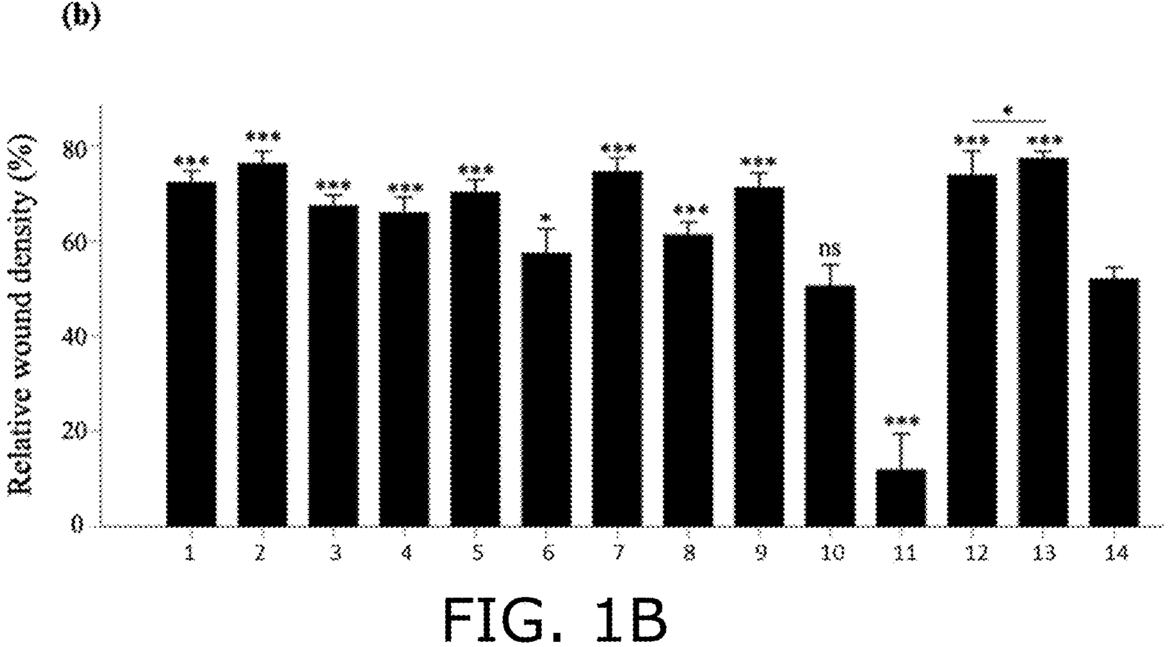

FIGS. 1A-1B. (a) Representative wound density comparison of human dermal fibroblasts incubated with exosomes from different plant sources after 50 h and (b) relative wound density quantification after 24 h. Media without exosomes was used as a control. Samples were compared to control and the migration rate was represented as relative wound density in percentage. Statistical analyses were performed using Student's t-test or ANOVA as appropriate and the results were considered significant when $p<0.05$: *$p<0.05$, ***$p<0.001$. Exosomes were isolated from 13 different plants: 1—ginger rhizome, 2—grape, 3—strawberry, 4—tomato, 5—cucumber, 6—apple, 7—olive, 8—celery, 9—soy, 10—grapefruit, 11—lemon peel, 12—cloudberry juice, 13—cloudberry callus. Sample 14 was the control sample. The results of the wound scratch assay showed that exosomes isolated from cloudberry stem cells culture promoted wound healing the most while exosomes extracted from other fruits, except lemon peel, also accelerated wound closure significantly.

Figure 2A:
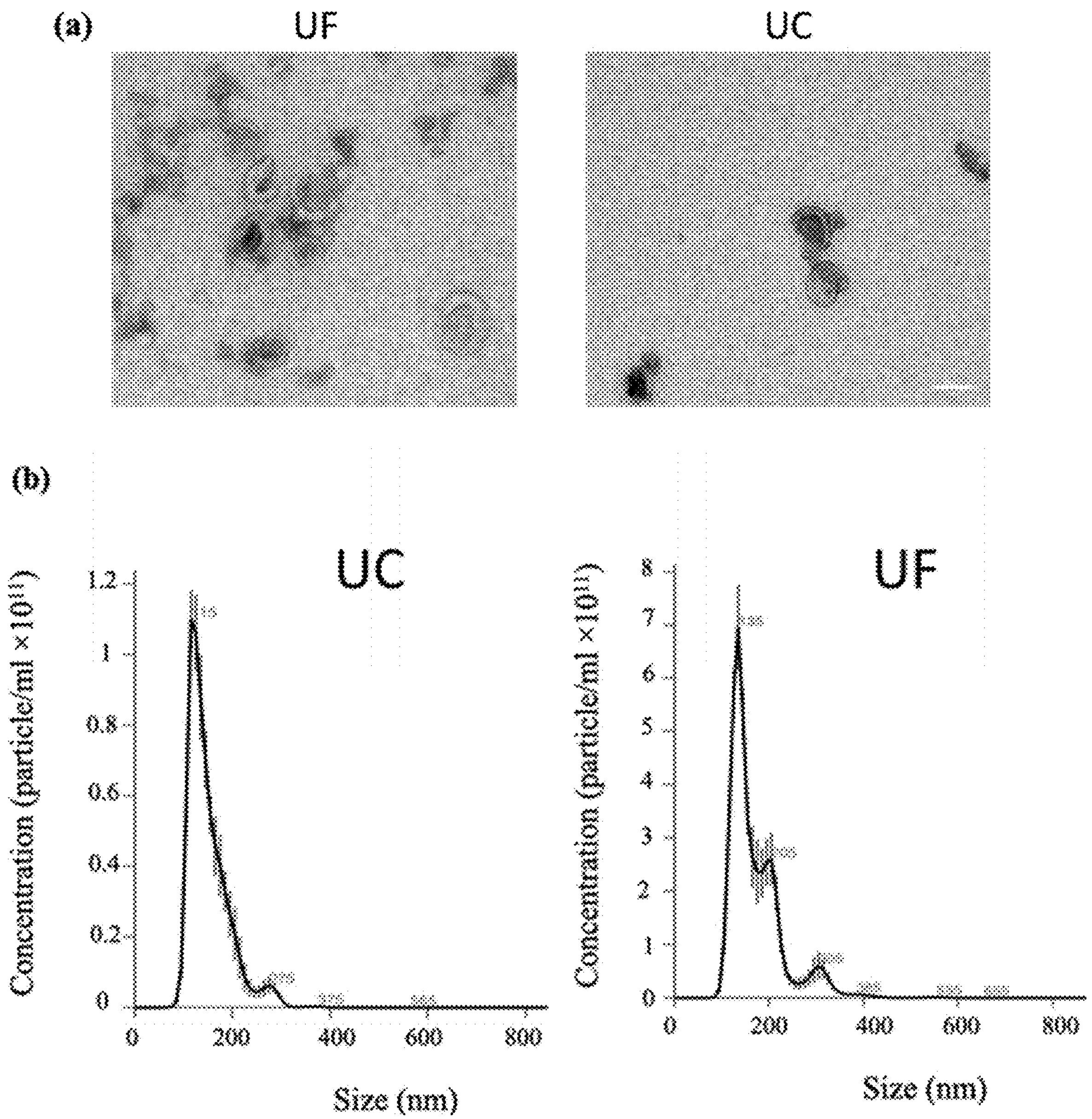
FIGS. 2A-2B illustrate the characterization of exosomes derived from apple juice isolated by ultrafiltration (UF) or ultracentrifugation (UC) as described in example 4: (a) representative images of transmission electron microscopy of isolated apple exosomes (scale bar=100 nm); (b) Size distribution analysis of isolated apple exosomes determined by NTA; (c) concentration and (d) size quantification of the exosomes using NTA; and (e) relative wound density of human dermal fibroblasts incubated for 24 hours with the exosomes.
Figure 2B:
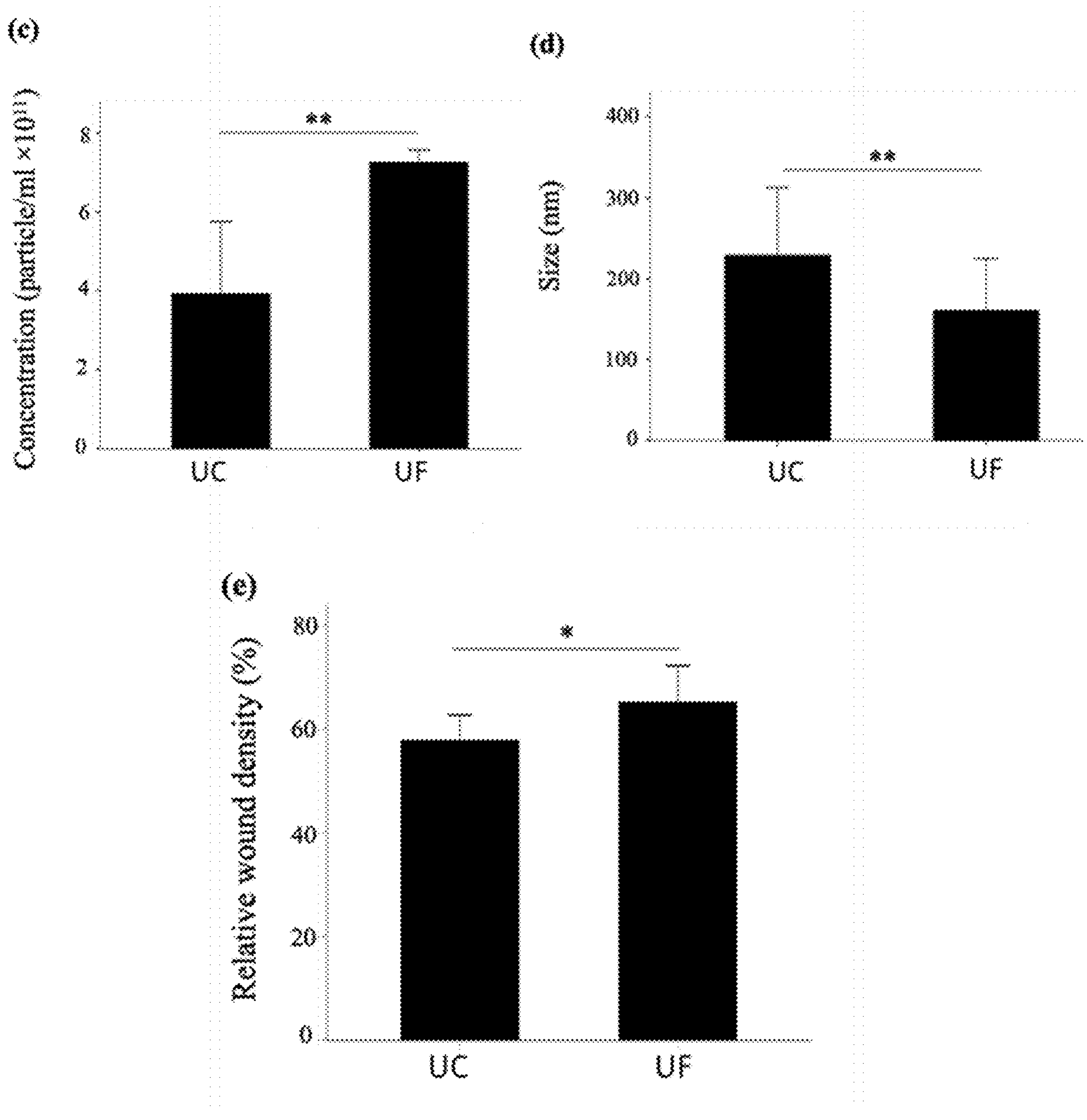

FIGS. 2A-2B. Characterization of exosomes derived from apple isolated by ultrafiltration (UF) or ultracentrifugation (UC). (a) Representative images of transmission electron microscopy of isolated apple exosomes. Scale bar=100 nm. (b) Size distribution analysis of isolated apple exosomes by UF or UC by NTA. (c) Concentration and (d) size quantification of isolated apple exosomes by UF or UC using NTA. (e) Relative wound density comparison of human dermal fibroblasts incubated for 24 hours with apple exosomes isolated by UF or UC. The migration rate is represented as relative wound density in percentage. Statistical analyses were performed using the ANOVA test and the results were considered significant when *$p<0.05$, **$p<0.01$. Data showed that isolated exosomes by UF resulted in a higher concentration of exosomes compared to UC by almost 45%. Furthermore, UC resulted in a bigger exosome size by almost 30%. These data may indicate a higher impact on exosome viability during UC compared to UF leading to protein aggregation, lower exosome concentration, and bigger exosomes size.

Figure 3A:
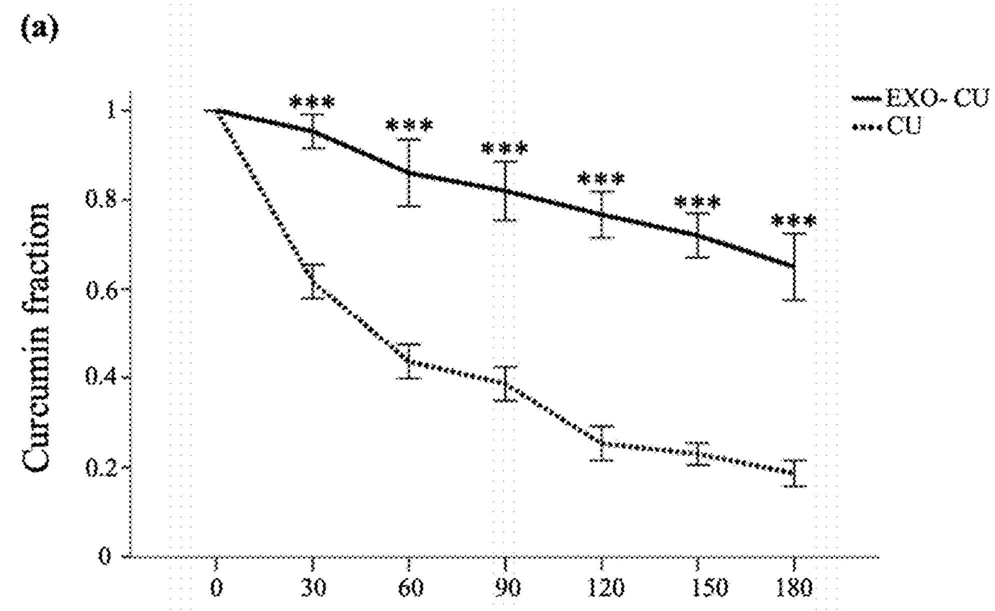
FIGS. 3A-3C represent the data as obtained in example 5: (a) quantification of curcumin concentration before and after encapsulation into the exosomes; (b) relative wound density of human dermal fibroblasts incubated for 48 hours with rehydrated lyophilized curcumin-loaded exosomes (5), rehydrated lyophilized apple exosomes (4), curcumin (3), DMSO (2) and no treatment (1); (c) representative images and (d) relative wound density quantification of human dermal fibroblasts following treatment with rehydrated lyophilized curcumin-loaded exosomes (5) and apple exosomes (4), curcumin (3), DMSO (2) and no treatment (1); (e) fibroblast proliferation measured by MTT colorimetric assay at 48 hours post-treatment with rehydrated lyophilized curcumin-loaded exosomes (5), rehydrated lyophilized apple exosomes (4), curcumin (3), DMSO (2) and no treatment (1).
Figure 3A:
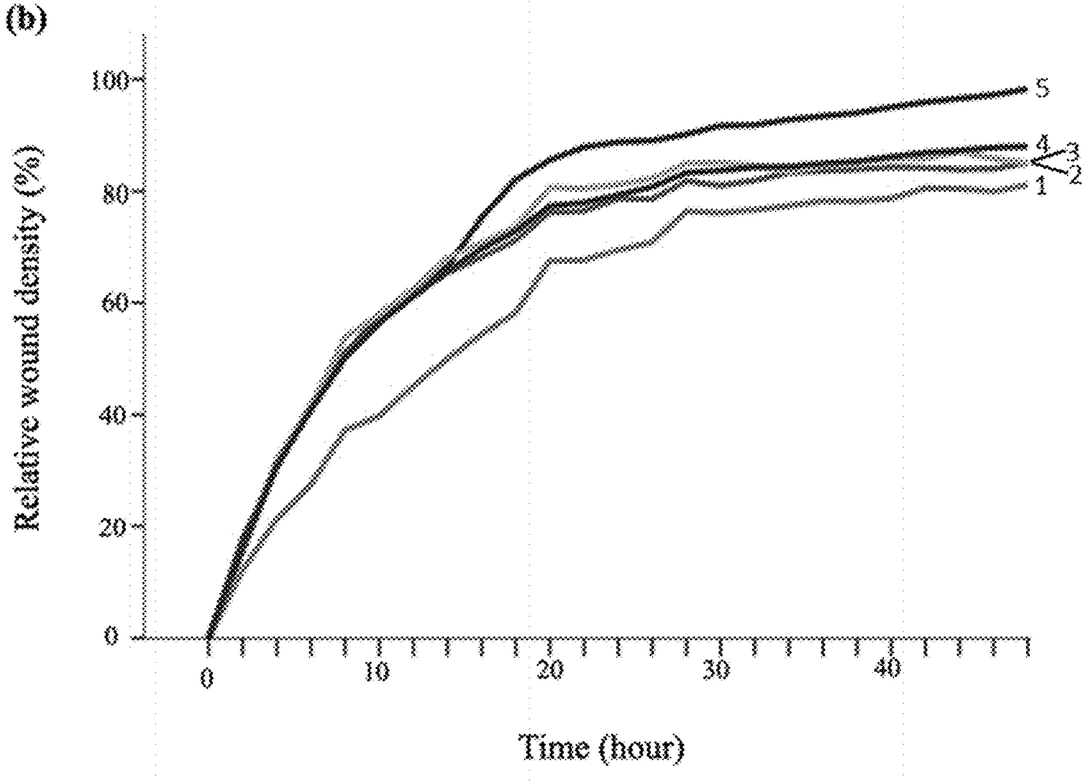
Figure 3B:
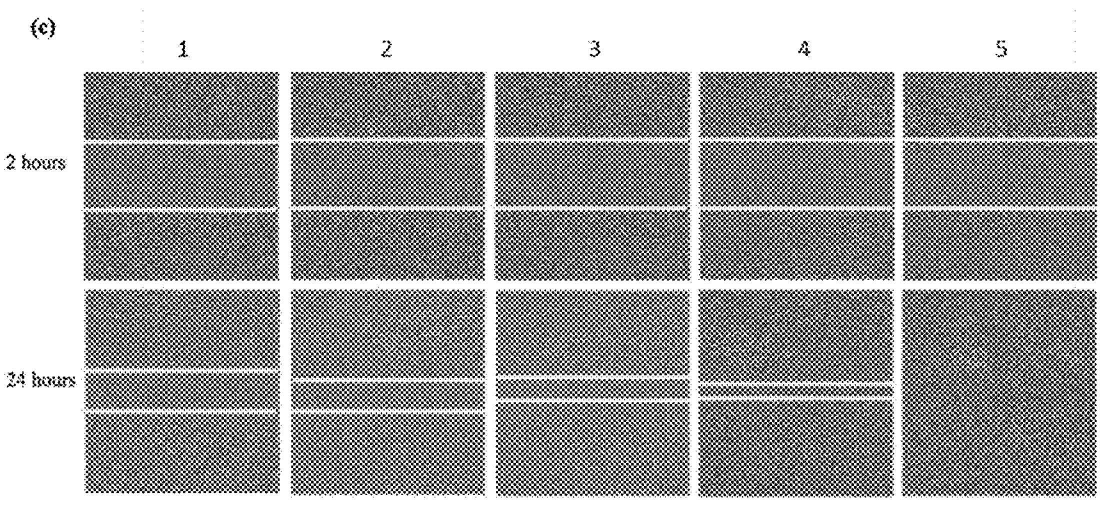
Figure 3B:
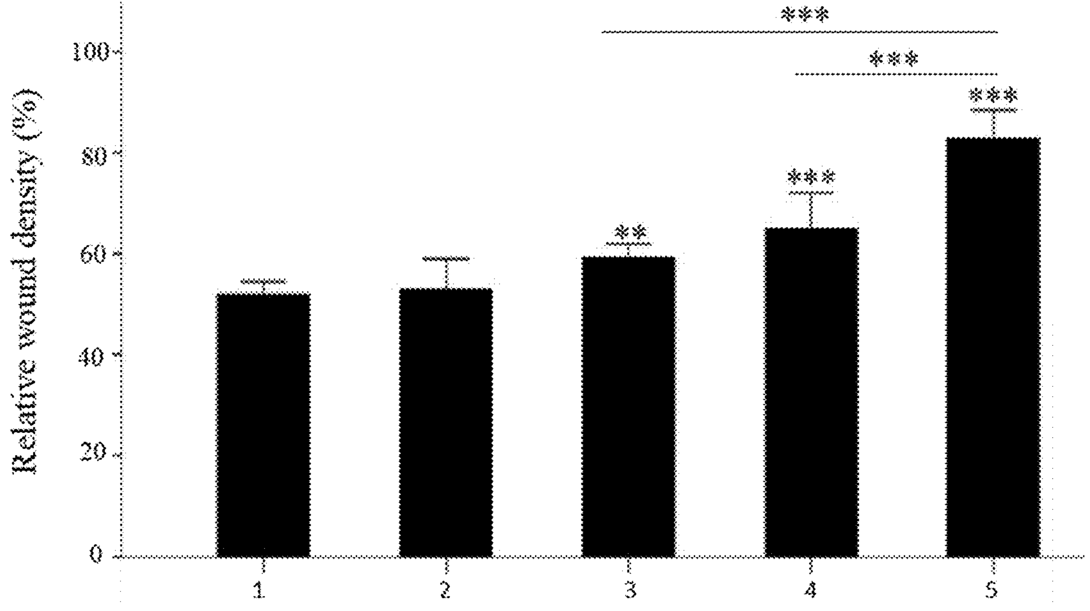
Figure 3C:
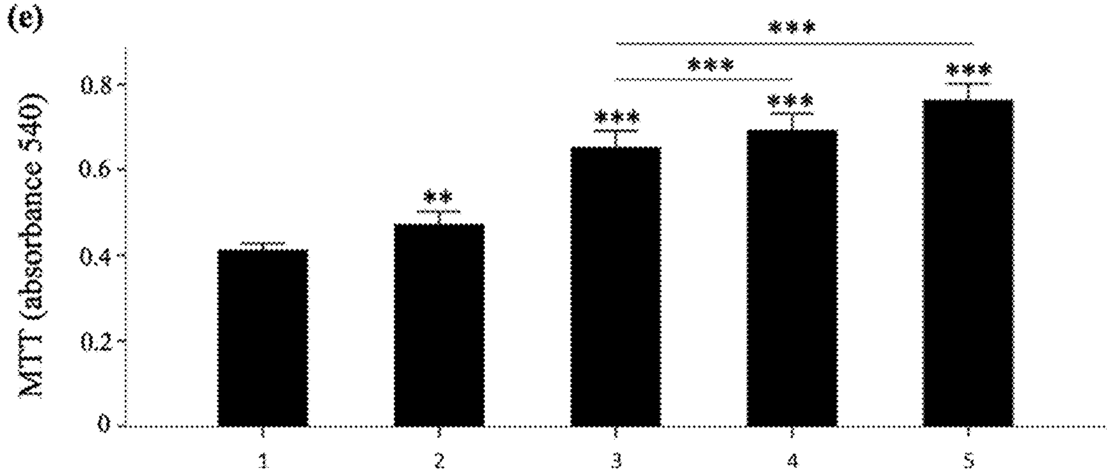

FIGS. 3A-3C. (a) Quantification of curcumin concentration before and after encapsulation into the exosomes. The initial concentration of curcumin was set as 1 and the reduction of the curcumin concentration was measured using a Nanodrop 1000 spectrophotometer at 420 nm and then compared to the encapsulated curcumin over time (minutes). (b) Relative wound density of human dermal fibroblasts incubated for 48 hours with rehydrated lyophilized curcumin-loaded exosomes (5), reconstituted lyophilised apple exosomes (4), and curcumin (3). DMSO (2) was used as a positive control. No treatment (1) was used as a negative control. (c) Representative images and (d) relative wound density quantification of human dermal fibroblasts following treatment with rehydrated lyophilized curcumin-loaded exosomes (5), reconstituted lyophilised apple exosomes (4), curcumin (3), and DMSO (2). Samples were compared to control (1) and migration rate was represented as relative wound density in percentage. (e) Human dermal fibroblast proliferation measurement by MU colorimetric assay at 48 hours post-treatment with rehydrated lyophilized curcumin-loaded exosomes (5), reconstituted lyophilised apple exosomes (4), curcumin (3), and DMSO (2). Statistical analyses were performed using the ANOVA test and the results were considered significant when $p<0.05$. $p<0.01$, *$p<0.001$. The results showed that encapsulation of curcumin into the exosomes increased curcumin's stability and bioactivity significantly. Furthermore, data showed that while all the treatments could enhance wound healing, curcumin-loaded plant exosomes accelerated the healing time the most by almost 45%. This data suggest that while plant exosomes can affect wound healing alone, they can at the same time be used as an efficient delivery system to increase bioavailability and enhance the delivery of active ingredients such as curcumin to the cells.

Figure 4:
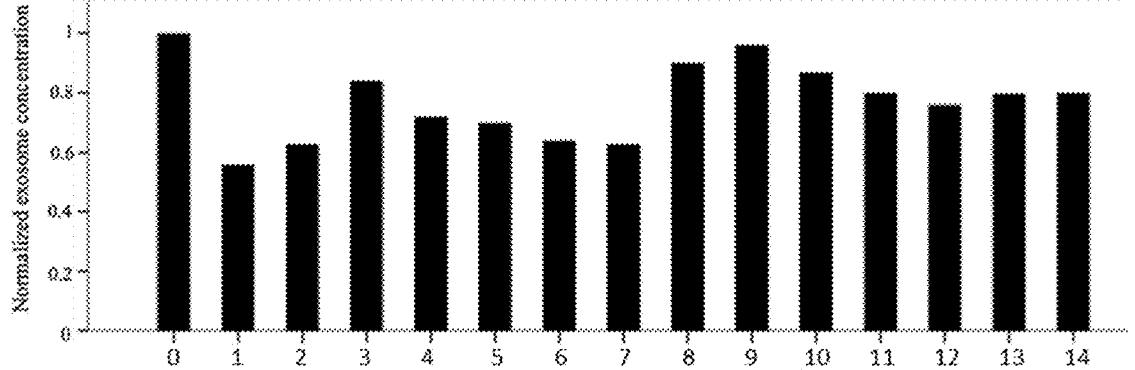
FIG. 4 illustrates the normalized concentration of exosomes after lyophilization using different cryoprotectant solutions as listed in Table 1 relative to the concentration prior lyophilization and measured using a BCA kit.

FIG. 4. The normalized concentration of lyophilized exosomes using different cryoprotectant solutions was measured by BCA kit. Samples 1 to 14 correspond to the cryoprotectant compositions listed in Table 1. Sample 0 corresponds to the starting exosome composition. While trehalose showed the best results as a single component cryoprotectant, the cryoprotectant solutions consisting of two components showed better results compare to single component cryoprotectants. Specifically, the combination of trehalose and LMW HA maintained 96% of the original exosome concentration before lyophilization.

Figure 5A:
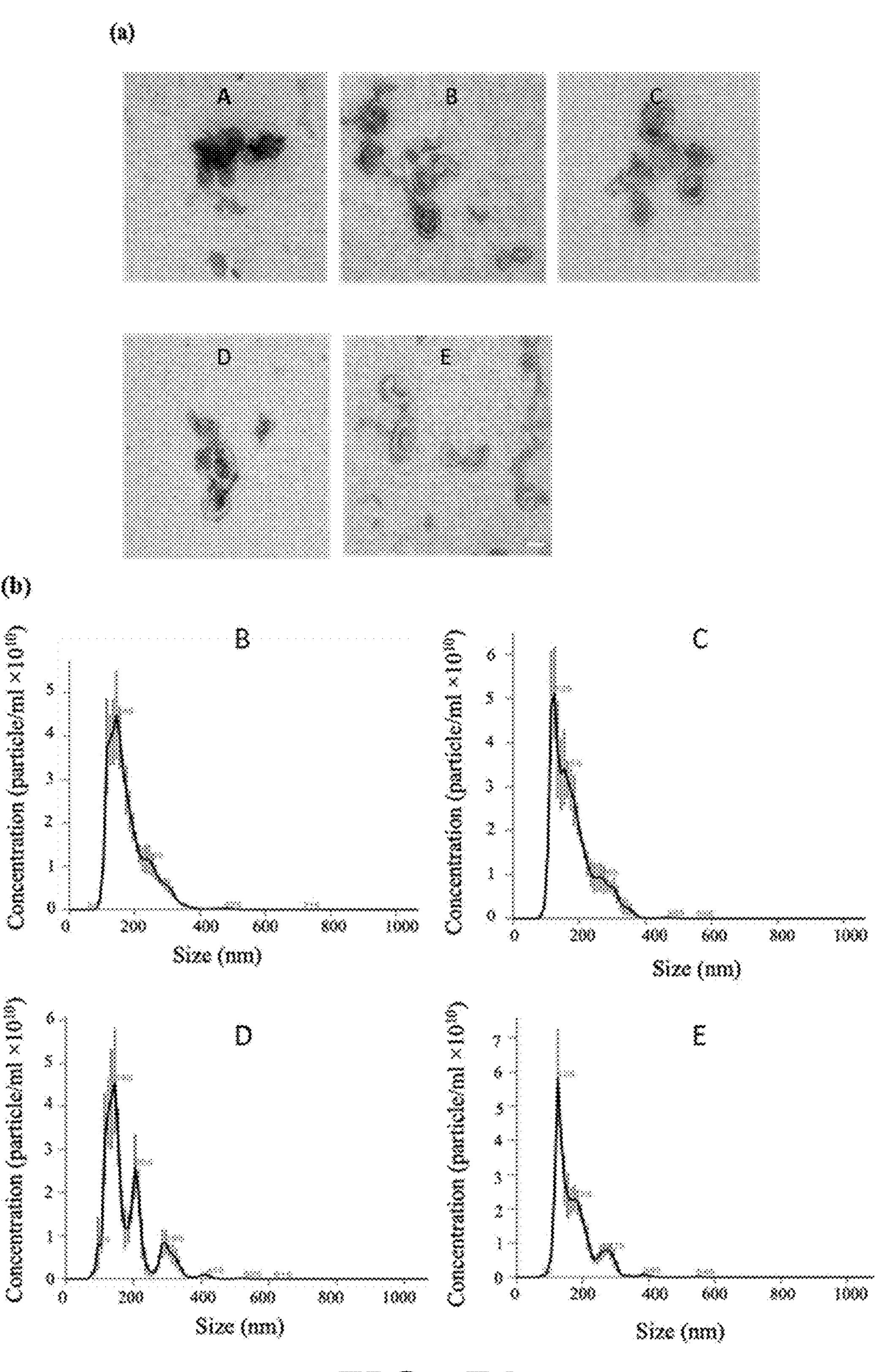
FIGS. 5A-5B illustrate the characterization of lyophilized apple exosomes using four different cryoprotectants (A—positive control (exosomes prior lyophilisation), A*—without cryoprotectant, B—2% trehalose, C—4% trehalose, D—5% LMW HA, and E—the combination of 2% trehalose+2.5% LMW HA): (a) representative images of transmission electron microscopy of lyophilized apple exosomes (scale bar=100 nm); (b) size distribution of lyophilized apple exosomes measured by Nanoparticle Tracking Analysis (NTA); (c) size and (d) concentration of lyophilized exosomes by NTA.
Figure 5B:
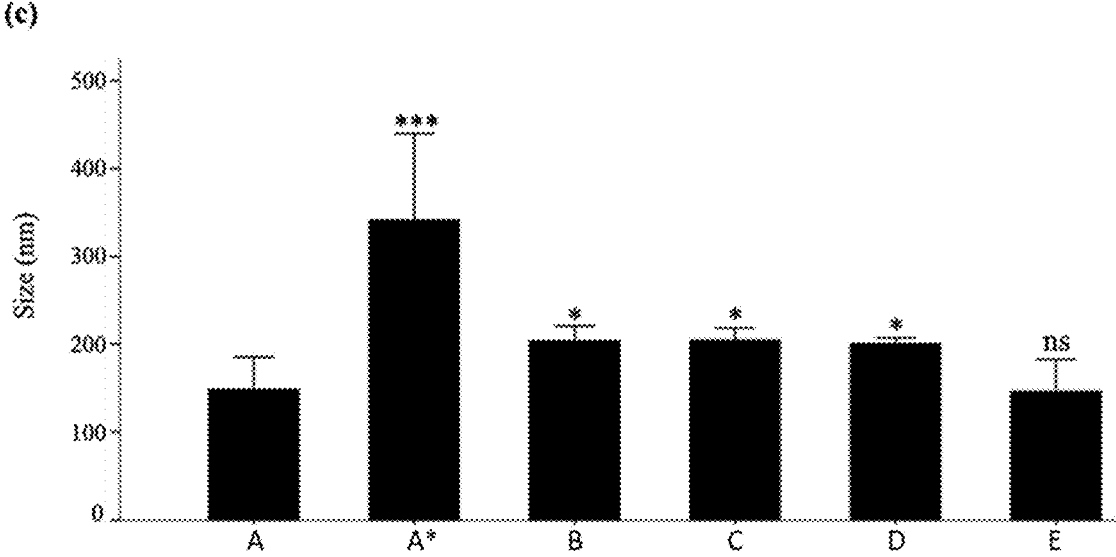
Figure 5B:
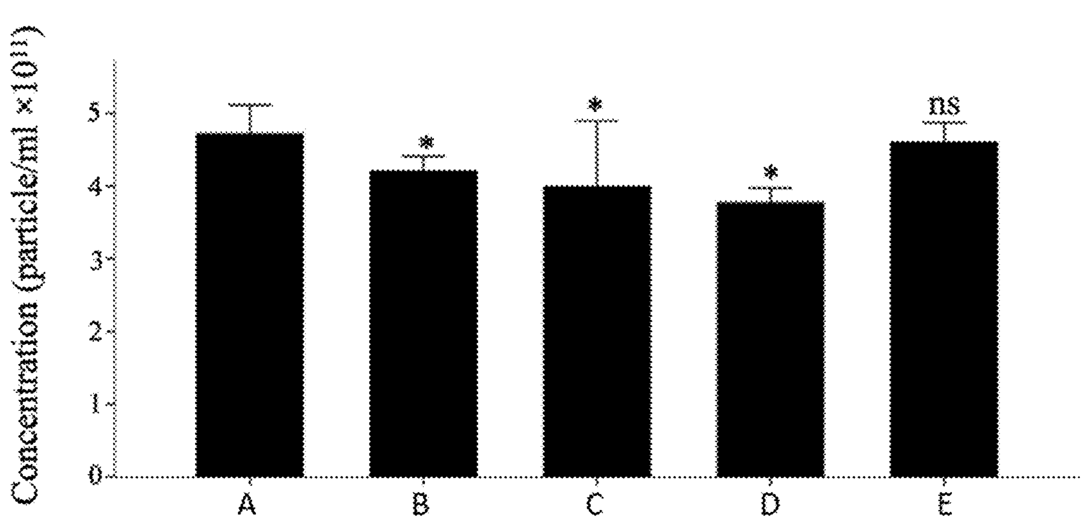

FIGS. 5A-5B. Characterization of lyophilized apple exosomes using four different cryoprotectants: B—2% trehalose, C—4% trehalose, D—5% LMW HA, and E—the combination of 2% trehalose+2.5% LMW HA. (a) Representative images of transmission electron microscopy of lyophilized apple exosomes. Lyophilized apple exosomes without cryoprotectants were used as a control in panel A. Scale bar=100 nm. (b) The size distribution of lyophilized apple exosomes was measured by Nanoparticle Tracking Analysis (NTA). (c) Size and (d) concentration quantification of lyophilized exosomes by NTA. Apple exosomes before lyophilization were used as a control A. A* is a negative control and shows the result of lyophilization in the absence of any cryoprotectant. Samples were compared to control. Statistical analyses were performed using the ANOVA test and the results were considered significant when $P<0.05$. *$P<0.05$, ***$P<0.001$, ns: non-significant. The results showed that cryoprotectants prevented the aggregation of exosomes during lyophilization significantly while best results were obtained by the combination of trehalose and LMW HA as cryoprotectants.

FIG. 6. Effect of lyophilized exosomes containing cryoprotectants including trehalose and LMW HA on fibroblasts' activity. (a) Relative wound density of human dermal fibroblasts, (b) human dermal fibroblasts' proliferation measurement by MTT colorimetric assay, and (c) collagen production by fibroblasts incubated with rehydrated lyophilized apple exosomes, lyophilized apple exosomes contain cryoprotectants and no treatments (control) after 48 h. Samples were compared to control and migration rate is represented as relative wound density in percentage. Statistical analyses were performed using the ANOVA test and the results were considered significant when $p<0.05$.$P<0.01$, *$P<0.001$. The results indicate the positive role of hyaluronic acid at low-molecular-weight in promoting fibroblasts' activity by enhancing their migration, proliferation, and extracellular matrix production such as collagen I.

Figure 7A:
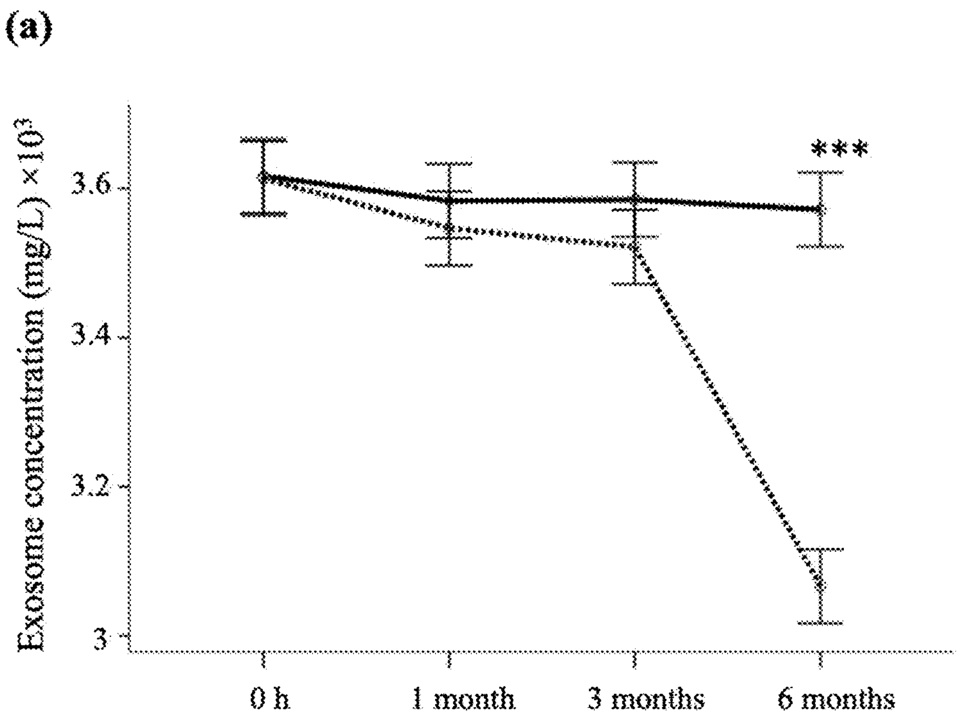
FIGS. 7A-7B illustrate the concentration of exosomes after storage lyophilised (solid lines) and non-lyophilized (dotted lines) exosomes at (a) −20° C., (b) +4° C. and (c) room temperature.
Figure 7A:
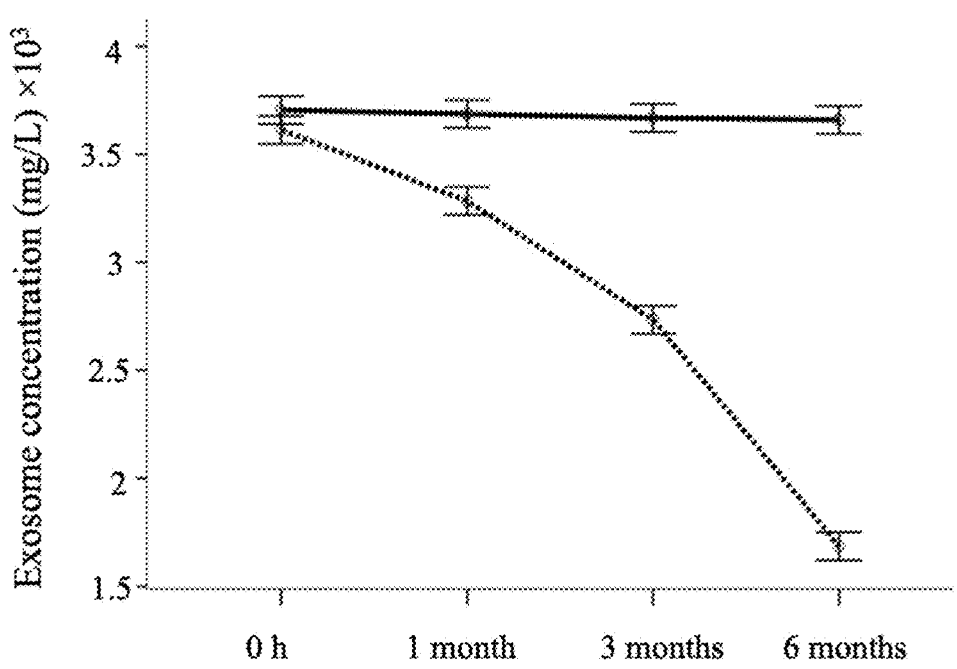
Figure 7B:
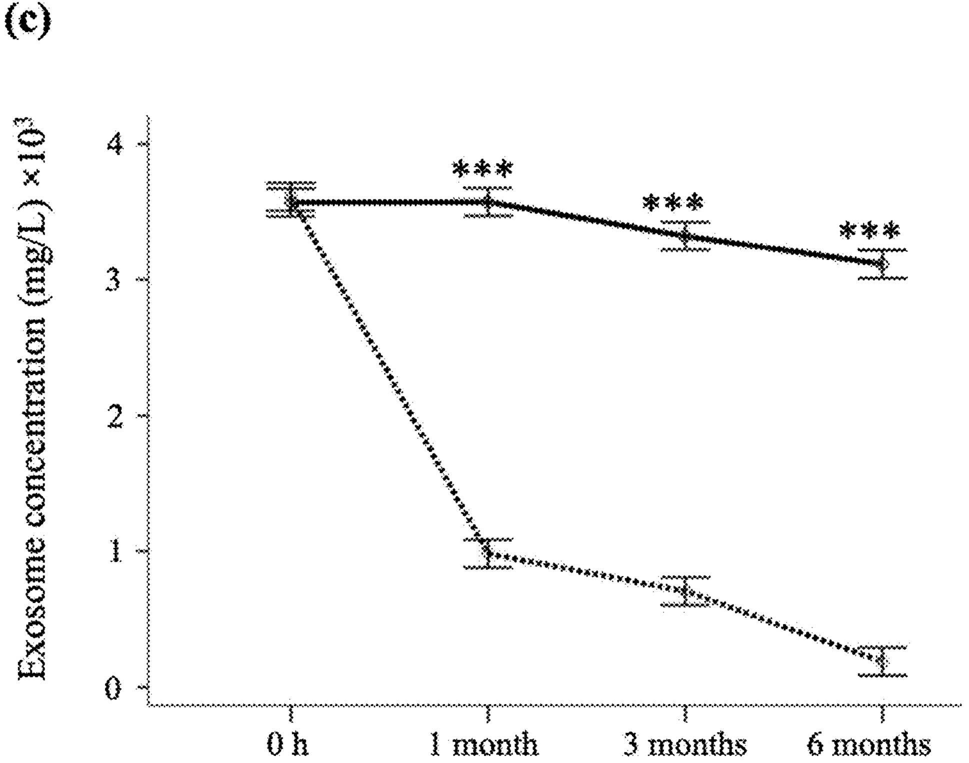

FIGS. 7A-7B. Exosomes retention of activity. The concentration of lyophilized exosomes (solid lines) and non-lyophilized exosomes (dotted lines) was measured by BCA kit at 0 h, 1 month, 3 months, and 6 months of lyophilization and isolation, respectively at (a) −20° C., (b) +4° C. and (c) room temperature. Lyophilized exosomes were rehydrated before performing the experiment. Both lyophilized and non-lyophilized exosomes were kept in −20° C., +4° C. and room temperature for a certain time before their concentration was measured. Statistical analyses were performed using the ANOVA test and the results were considered significant when $p<0.05$. $p<0.01$, *$p<0.001$. Data showed that the concentration of non-lyophilized exosomes significantly dropped over time while the protein content of lyophilized exosomes is stable over time while exposed to different temperatures.

FIG. 8. Exosomes viability in different pH environments. Re-hydrated lyophilized exosomes were kept in PBS at three different acidities including 3.5 (acidic), 7 (neutral), and 10 (basic) for 2 hours. The exosome concentration was then measured by NTA. Statistical analyses were performed using the ANOVA test and the results were considered significant when $p<0.05$. $p<0.01$, *$p<0.001$. Data from pH=7 and pH=10 was compared to data from pH=3.5 as the optimum condition. Data show that while acidic pH can maintain exosome viability the most, basic pH decreases exosome viability by 88% compared to acidic pH.

FIG. 9. Schematic design of packaging for a skincare formulation containing exosomes. The packaging device is an airless bottle with at least two separated compartments, i.e. a liquid powder mixing airless bottle, is used wherein the freeze-dried powder containing exosomes is located in a powder compartment (A) while the liquid of the formulation was located in a water compartment (B).

The invention claimed is:

1. A cryoprotectant for exosomes comprising trehalose and low molecular weight hyaluronic acid (LMW HA) having molecular weight lower than 10 kDa wherein:
- the w/w ratio of trehalose to low molecular weight hyaluronic acid is between 0.3 and 0.7, the concentration in the combined exosome cryoprotectant preparation of trehalose is at least 25 mM and/or at most 100 mM, and/or
- the concentration in the combined exosome cryoprotectant preparation of LMW HA is at least 1% (w/v) and/or at most 5% (w/v),
- which provides enhanced exosome stability and bioactivity after storage, of a smaller homogeneous, and higher concentration of exosomes compared to LMW HA and trehalose alone.

2. A freeze-dried composition comprising exosomes, low molecular weight hyaluronic acid (LMW HA) having molecular weight lower than 10 kDa and trehalose wherein:
- the w/w ratio of trehalose to low molecular weight hyaluronic acid is between 0.3 and 0.7, the concentration in the combined exosome cryoprotectant preparation of trehalose is at least 25 mM and/or at most 100 mM, and/or
- the concentration in the combined exosome cryoprotectant preparation of LMW HA is at least 1% (w/v) and/or at most 5% (w/v),
- which provides enhanced exosome stability and bioactivity after storage, of a smaller homogeneous, and higher concentration of exosomes compared to LMW HA and trehalose alone.

3. A production process for the composition of claim 2 comprising the steps of:
- (a) providing an exosome containing liquid,
- (b) combining the exosome containing liquid with a cryoprotectant comprising trehalose and low molecular weight hyaluronic acid to obtain a combined exosome cryoprotectant preparation, and, (c) freeze drying the combined exosome cryoprotectant preparation wherein:

the w/w ratio of trehalose to low molecular weight hyaluronic acid is between 0.3 and 0.7, the concentration in the combined exosome cryoprotectant preparation of trehalose is at least 25 mM and/or at most 100 mM, and/or the concentration in the combined exosome cryoprotectant preparation of LMW HA is at least 1% (w/v) and/or at most 5% (w/v), which provides enhanced exosome stability and bioactivity after storage, of a smaller homogeneous, and higher concentration of exosomes compared to LMW HA and trehalose alone.

4. The cryoprotectant according to claim 1, wherein the exosomes are plant derived exosomes (PDEs).

5. The production process according to claim 3, wherein the exosomes are plant derived exosomes (PDEs).

6. The production process of claim 5, wherein the exosome containing liquid is provided by a method comprising:

providing a homogenised plant cell preparation containing the plant derived exosomes, and, subjecting the plant cell preparation to a filtration process comprising at least one ultrafiltration step using a filter membrane having a cut-off smaller than or equal to 10 kDa.

7. The production process of claim 6, wherein the filtration process further comprises prior to at least one ultrafiltration one or more of:

filtering the homogenised plant cell preparation through a juice filter net and retaining resulting liquid, centrifugation of the homogenised plant cell preparation or resulting liquid at least 400×g for at least 10 minutes and retaining the supernatant, and, filtering the homogenised plant cell preparation, the supernatant or resulting liquid through a membrane filter with a pore size of 0.2 μm.

8. The cryoprotectant according to claim 1, wherein the exosomes are plant derived exosomes from a plant selected from cloudberry, grape, grapefruit, strawberry, raspberry, blueberry, apple, cucumber, tomato, olive, celery, lemon, ginger or soy.

9. The freeze-dried composition according to claim 2, wherein the exosomes are plant derived exosomes from a plant selected from cloudberry, grape, grapefruit, strawberry, raspberry, blueberry, apple, cucumber, tomato, olive, celery, lemon, ginger or soy.

10. The cryoprotectant according to claim 1, wherein the exosomes are plant derived exosomes isolated from plant juice or plant callus tissue.

11. The freeze-dried composition according to claim 2, wherein the exosomes are plant derived exosomes isolated from plant juice or plant callus tissue.

12. The cryoprotectant according to claim 1, wherein the exosomes are plant derived exosomes from cloudberry callus.

13. The freeze-dried composition according to claim 2, wherein the exosomes are plant derived exosomes from cloudberry callus.

14. The cryoprotectant according to claim 1, wherein the exosomes are loaded with an active ingredient.

15. The freeze-dried composition according to claim 2, wherein the exosomes are loaded with an active ingredient.

16. A skincare product comprising the freeze-dried composition according to claim 2.

17. The freeze-dried composition for use according to claim 2, wherein the freeze-dried composition is applied to the skin using a dermatologically acceptable liquid excipient.

18. The freeze-dried composition for use according to claim 2, wherein the freeze-dried composition is administered to the skin by means of a two-compartment dispensing device containing the freeze-dried composition in one compartment and the liquid excipient in a second compartment, and, wherein the freeze-dried composition is mixed with the liquid excipient upon dispensing the skincare product to the skin.

19. The freeze-dried composition for use according to claim 18, wherein the liquid excipient further comprises a skin penetration enhancer selected from terpenes, and fatty acids containing 1,8-cineole, d-limonene, and l-menthol.

* * * * *